(12) United States Patent
Osborne et al.

(10) Patent No.: US 7,906,456 B2
(45) Date of Patent: Mar. 15, 2011

(54) FILTRATION MEDIA HAVING A CHEMICAL REAGENT

(75) Inventors: Michael W. Osborne, Louisville, KY (US); Zhong C. He, Suzhou (CN); Ng Cheah Wei, Selangor (MY)

(73) Assignee: AAF-McQuay Inc., Louisville, KY (US)

( * ) Notice: Subject to any disclaimer, the term of this patent is extended or adjusted under 35 U.S.C. 154(b) by 883 days.

(21) Appl. No.: 11/627,465

(22) Filed: Jan. 26, 2007

(65) Prior Publication Data

US 2008/0182748 A1    Jul. 31, 2008

(51) Int. Cl.
*B01J 20/08*    (2006.01)
*C01F 7/02*    (2006.01)
(52) U.S. Cl. .................. 502/414; 423/625; 502/415
(58) Field of Classification Search .................. 423/625; 502/415, 414
See application file for complete search history.

(56) References Cited

U.S. PATENT DOCUMENTS

| | | | |
|---|---|---|---|
| 3,049,399 A | 8/1962 | Gamson et al. |
| 3,226,332 A | 12/1965 | Lincoln et al. |
| 4,482,641 A | 11/1984 | Wennerberg |
| 4,637,408 A | 1/1987 | Rainer et al. |
| 4,831,003 A | 5/1989 | Lang et al. |
| 4,855,276 A | 8/1989 | Osborne et al. |
| 4,970,189 A | 11/1990 | Tachibana |
| 5,200,092 A | 4/1993 | Richards et al. |
| 5,336,431 A | 8/1994 | Richards et al. |
| 5,891,221 A | 4/1999 | Rohrbach et al. |
| 5,948,398 A | 9/1999 | Hanamoto et al. |
| 5,997,829 A | 12/1999 | Sekine et al. |
| 6,004,522 A | 12/1999 | England |
| 6,858,192 B2 | 2/2005 | Graham et al. |
| 6,986,806 B2 | 1/2006 | Kvietok et al. |
| 7,157,030 B2 | 1/2007 | Rintoul |
| 2005/0144918 A1 | 7/2005 | Rintoul |

FOREIGN PATENT DOCUMENTS

| WO | 9516518 A1 | 6/1995 |
| WO | 2004047950 A1 | 6/2004 |

*Primary Examiner* — Stanley Silverman
*Assistant Examiner* — James A Fiorito
(74) *Attorney, Agent, or Firm* — Middleton Reutlinger; John F. Salazar (57) ABSTRACT

An odor filtration media having a chemical reagent which removes odor causing fluid contaminants from a fluid stream through the use of granular or shaped media have a chemical composition including permanganate is provided. A method of producing the odor absorbing media having a chemical reagent is also provided and comprises the steps of mixing $H_2O$, $KMnO_4$, and at least one salt adding ions or ionic compounds selected from the group consisting of $Na^+$, $Li^+$, $K^+$, $NH_4^+$, $Cl^-$, $SO_4^{2-}$, $BO_3^{2-}$, $CO_3^{2-}$, $PO_4^{3-}$, $NO_3^-$ and combinations thereof, or from the group consisting of $Na^+$, $Li^+$, $K^+$, $NH_4^+$, $Mg^{2+}$, $Ca^{2+}$, $Cl^-$, $BO_3^{2-}$, $NO_3^-$ and combinations thereof, forming an impregnating solution. The impregnating solution is heated and combined with a support material to form a coherent mass.

5 Claims, 4 Drawing Sheets

Additives Effect on Media

| Example | Formulation | | | | | | Test Data | | | | |
|---|---|---|---|---|---|---|---|---|---|---|---|
| | AA g | KMnO₄ g | NaHCO₄ g | NaNO₃ g | Na₃PO₄ g | Hardness g | Abrasion % | Moisture % | H₂O Leaching Test (min) | Gas/Capacity g/cc |
| 1 | 100 | 15 | 15 | 15 | | 51 | 11.05 | 15.09 | 215 | 0.03782 |
| 2 | 100 | 15 | | 15 | 5 | 21 | 1.98 | 14.92 | 260 | 0.02581 |
| 3 | 100 | 15 | 15 | 15 | 5 | 52 | 1.09 | 15.11 | 260 | 0.02581 |
| 4 | 100 | 15 | 15 | | 5 | 27 | 8.51 | 14.89 | 200 | 0.03728 |
| 5 | 100 | 15 | 15 | 10 | 5 | 69 | 1.2 | 14.98 | 180 | 0.04852 |
| 6 | 100 | 15 | 15 | 5 | | 45 | 1.01 | 13.27 | 195 | 0.04594 |
| 7 | 100 | 15 | 15 | 10 | | 61 | 0.99 | 10.63 | 245 | 0.02902 |
| 8 | 100 | 15 | 15 | 5 | 5 | 52 | 1.06 | 13.18 | 240 | 0.02917 |
| 9 | 100 | 15 | 15 | 5 | 5 | 58 | 1.05 | 10.33 | 285 | 0.02304 |
| 10 | 100 | 15 | 15 | 5 | 2 | 44 | 1.08 | 11.72 | 220 | 0.03072 |
| 11 | 100 | 15 | 15 | 10 | 2 | 58 | 1.02 | 13.95 | 225 | 0.0294 |
| 12 | 100 | 15 | 15 | 15 | 2 | 41 | 1.05 | 10.13 | 230 | 0.03064 |
| 13 | 100 | 15 | 15 | | 2 | 38 | 1.07 | 11.01 | 190 | 0.04614 |
| 14 | 100 | 15 | 15 | 15 | | 55 | 1.01 | 10.95 | 219 | 0.02484 |
| 15 | 100 | 10 | 15 | | | 53 | 1.73 | 14.88 | 224 | 0.03446 |
| Average of Examples 1 - 14 | | | | | | 48 | 2.37 | 12.87 | | |

FILTRATION MEDIA HAVING A CHEMICAL REAGENT

CROSS-REFERENCE TO RELATED APPLICATIONS

Not applicable.

STATEMENT REGARDING FEDERALLY SPONSORED RESEARCH OR DEVELOPMENT

Not applicable.

FIELD OF INVENTION

The present invention relates to filters, such as fluid or air filters, utilizing a solid filtration media having a chemical reagent for odor removal.

BACKGROUND OF THE INVENTION

It is well known to use activated materials such as activated charcoal in an air stream in an attempt to remove odors. Conventional carbon adsorbents have been found to have a broad range of effectiveness against odors. However, such activated carbon adsorptive techniques of removing odor from an air stream are effective only for a relatively short time period, are relatively inefficient at low odor concentration levels, have performance which declines rapidly at higher relative humidities, and frequently result in a relatively high pressure differential across the activated carbon filter media. Odors are adsorbed onto and into the pores of the charcoal. These adsorbed odors are desorbed to varying degrees by such conditions as temperature changes, the super saturation of the adsorptive surfaces, and by preferentially adsorbed gases and vapors. This action occurs to a greater or lesser degree with all adsorbent materials resulting in the production of a desorbed odor complex atypical of the original adsorbed odor. As a result relatively large quantities of activated carbon are required in such filter devices; however, even with the larger amount of activated carbon the relatively large pressure differential problem remains.

The use of activated forms of alumina as a support in gas filters is known. Activated aluminas have been coated and or impregnated with various agents by methods of varying complexities. The principal problem in impregnating active alumina has been to economically impregnate the alumina with an effective chemical composition while maintaining the desired degree of activity and resistance to abrasion, without destruction of the impregnant material or support. Materials which are particularly difficult to impregnate into active alumina while maintaining sufficient strength and desired properties are the permanganates of alkali metals, notably potassium permanganate. However, permanganate ions have rapid reaction kinetics and a broad reaction profile for inorganic and organic moieties and therefore have long been used in odor removal in liquid scrubber applications and in dry supported forms. They also have a history of demonstrated performance for a wide range of odors. Permanganate ions are strong oxidizing agents capable of reacting with aldehydes, reduced sulfur compounds, unsaturated hydrocarbons, alcohols, phenols, amines, hydrogen sulfide, sulfur dioxide, etc. Therefore it is desirable to have a filter media with a support material impregnated with permanganate.

Early development work to produce satisfactory activated alumina forms containing an oxidizer such as permanganate generally involve pelletizing the alumina starting material, then evacuating the alumina pellets to clear the pores so that the alumina forms could be effectively impregnated with an oxidizing agent. Impregnation of the alumina forms has typically been accomplished by spraying the forms with an impregnating solution. After impregnation with the oxidizing agent, the alumina forms are dried to remove uncombined water. Among the problems encountered in attempting to adapt presently used commercial procedures for the production of permanganate impregnated alumina composites has been the difficulty to obtain the desired uniform distribution of the oxidizing agent throughout the alumina mass. Furthermore, the economical formation of filter media having a desired concentration of permanganate, a desired pellet size or shape, and a desired physical strength has remained a challenge.

SUMMARY OF THE INVENTION

An impregnated pellet, preferably alumina-based, and the method of producing same wherein the pellet is impregnated with at least one oxidizing agent having permanganate, for use in treating fluid streams is provided. The permanganate is impregnated in the alumina-based, particle, pellet, tablet, or other media having a desired shape at a concentration in a cost effective manner and placed into a filter cartridge, used in bulk form, mechanically or adhesively attached to a substrate such as a foam, wire, synthetic fibers, and fiberglass, or contacted with a fluid stream by other means as is known by persons having ordinary skill in the art for the removal of odors from a fluid stream. At least a portion of the permanganates are placed into an impregnating solution in the form of a lower cost permanganate source such as potassium permanganate. Water and various salts are also introduced into the impregnating solution adding ions and ionic compounds such as $Na^+$, $Li^+$, $K^+$, $NH_4^+$, $Mg^{2+}$, $Ca^{2+}$, $Cl^-$, $SO_4^{2-}$, $BO_3^{2-}$, $CO_3^{2-}$, $PO_4^{3-}$, $NO_3^-$, and combinations thereof, increasing the solubility of the permanganate in the impregnating solution, introducing additional odor reducing agents, and/or increasing the hardness or physical strength of the formed tablets, pellets, or other shaped media. Preferably, an alumina-based pellet or tablet is made and impregnated with the impregnating solution by mixing the impregnating solution having potassium permanganate with activated alumina and forming into a desired shape.

Other features of the present invention will become apparent upon reviewing the following detailed description of the invention, in conjunction with the drawing and the appended claims.

BRIEF DESCRIPTION OF THE DRAWINGS

Reference to the figures discloses an embodiment of a filter media cartridge and test data of filter media having a chemical reagent and are not to be interpreted as limiting the scope of the present invention as other cartridges, cassettes, substrates, and other means for containing or supporting the filter media and compositions of the filter media will become known by persons having ordinary skill in the art upon a reading of the present disclosure.

DETAILED DESCRIPTION

The present invention relates to a chemical reagent for the removal of odors from a fluid, typically air in an enclosed environment. Odor removal is accomplished by passing the fluid through the filter media contained in a filter cartridge or other media retaining device or supporting material such as mechanical or adhesive attachment of the filter media to a substrate like a foam, wire, synthetic fibers, fiberglass, etc., or other means of contacting fluid with the filter media as is known in the art, wherein odors are oxidized. Permanganates oxidize odors such as those emitted by hydrogen sulfide and organics, swiftly and efficiently, converting the sulfides and organics into non-odorous oxidation products, therefore permanganate is incorporated into the filter filtration media. The filter media comprises an activated hydrophilic substrate having permanganate impregnated therein. The substrate may include silica alumina, gel, activated bauxite, and activated clays. Preferably the substrate includes activated alumina. Permanganate is known to oxidize a majority of odors such as tobacco, body, and cooking odors, to carbon dioxide, water or some other odorless oxidation product. An amount of water in the substrate is necessary for the oxidation reaction to take place. Without water, the permanganate will not ionize to release the active permanganate ions. It is for this reason that the filter media comprises a hydrophilic substrate, preferably alumina.

Preferably the substrate has a substantial portion of alumina in the form of a pellet, tablet, particle, or other shaped as is known in the art. A media and method of producing such media is provided wherein the media is impregnated with at least one oxidizing agent having permanganate for use in treating fluid, preferable air, streams. The permanganate is impregnated in a pellet, tablet, or other shaped media, at a desired concentration, in a cost effective manner, forming filtration media having a desired hardness, and placed into a fluid stream for the removal of odors therefrom. Permanganates are preferably impregnated into the substrate in the form of permanganates of $Na^+$, $Li^+$, $K^+$, $NH_4^+$, $Mg^{2+}$, and/or $Ca^{2+}$.

Advantageously, an activated alumina base is substantially uniformly impregnated with metal permanganate salt. A method of making the filter media involves first providing an activated alumina support material. Activated alumina is commercially available in micro-granular form. By providing a micro-granular activated alumina of predetermined particle size distribution, it is possible to obtain pellets, tablets, or other shaped media of improved strength and other physical properties as well as more uniform impregnation of the finished alumina containing based media. The activated alumina is preferably capable of rehydration. The activated alumina is then mixed with an impregnating solution having metal permanganate salts resulting in alumina containing permanganate substantially uniformly distributed throughout. When forming media by compression, the alumina containing permanganate is partially cured under conditions of heat and humidity forming a coherent mass. The addition of water to account for both hydration and solubilization is necessary for keeping the permanganate in solution, as insoluble permanganate are not reactive. It is necessary not to allow curing to proceed to completion when the partially hydrated materials are to be reshaped, as when forming media with compression, as the impregnated particles will lack the chemical bonding necessary to provide the formed media with desired properties of strength and abrasion resistance. When forming media by compression, the partially cured coherent mass is ground into granules, preferably having a particle size of about 40 to 80 mesh, and compressed into a desired shape. Curing is completed after the media is formed. Hydration and curing may be conducted before and/or during pelletization to obtain the desired characteristics of strength and open pore volume.

Impregnation of the alumina with the permanganate can be performed either prior to pelletization, during pelletization or after pelletization and is typically accomplished by mixing the alumina, preferably micro-granular activated alumina, with a permanganate containing impregnating solution in a manner to substantially uniformly distribute the permanganate throughout the alumina substrate. This is typically accomplished by mechanical mixing of the alumina substrate in a solution having permanganate salts and water. The permanganate is absorbed into the alumina substrate. The amount of permanganate absorbed into the alumina substrate is predictable with the concentration of the permanganate in the solution. When a permanganate solution is contacted with a solid material, for example alumina, the amount of permanganate absorbed is proportional to the concentration of the permanganate in the solution. Therefore, a higher solubility of the permanganate in solution will yield a higher concentration of the permanganate in the finished media, consequently having a higher oxidation capacity. However, the more economical source of permanganate, the potassium salt of permanganate, has solubility in water of only about 4% (wt/v) at room temperature while a less economical source of permanganate, the sodium salt of permanganate, has a much higher solubility in water exceeding 40% (wt/v) at room temperature. Preferably, the impregnating solution of the present invention has permanganate in solution at a concentration of at least 20% (wt/v), and higher concentration being desirable.

The introduction of one or more ions or ionic compounds such as $Na^+$, $Li^+$, $K^+$, $NH_4^+$, $Mg^{2+}$, $Ca^{2+}$, $Cl^-$, $SO_4^{2-}$, $BO_3^{2-}$, $CO_3^{2-}$, $PO_4^{3-}$, $NO_3^-$, and combinations thereof into a potassium permanganate containing solution improves the solubility of the permanganate in the solution by forming various permanganate salts therein. However, it is important to note that the addition of $Mg^{2+}$ or $Ca^{2+}$ with $CO_3^{2-}$, as carbonate or bicarbonate, or $Mg^{2+}$ or $Ca^{2+}$ with $SO_4^{2-}$, as sulfate or bisulfate, or $Mg^{2+}$ or $Ca^{2+}$ with $PO_4^{3-}$, as phosphate or other causes undesired precipitation of $MgCO_3$, $CaCO_3$, $Mg_3(PO_4)_2$, $Ca_3(PO_4)_2$, $MgSO_3$, or $CaSO_3$, therefore these combinations are to be avoided. Therefore, mixing $H_2O$, $KMnO_4$, and at least one salt adding ions or ionic compounds selected from the group consisting of $Na^+$, $Li^+$, $K^+$, $NH_4^+$, $Cl^-$, $SO_4^{2-}$, $BO_3^{2-}$, $CO_3^{2-}$, $PO_4^{3-}$, $NO_{3-}$ and combinations thereof, or from the group consisting of $Na^+$, $Li^+$, $K^+$, $NH_4^+$, $Mg^{2+}$, $Ca^{2+}$, $Cl^-$, $BO_3^{2-}$, $NO_3^-$ and combinations thereof, form an impregnating solution having an increase in solubility of permanganate. For example, the introduction of sodium cations into a potassium permanganate containing solution improves the solubility of the permanganate in the solution by forming sodium permanganate salt therein. Sodium permanganate salt is much more hydroscopic than potassium permanganate salt. Since sodium permanganate has a cost premium on a dry basis over potassium permanganate of a factor of about two or more, the introduction of sodium cations from sodium nitrate, sodium carbonate, sodium bicarbonate, sodium chloride, etc., allows for a more economical concentrated permanganate solution than can be achieved with the use of potassium permanganate alone. This solution may have a base or acid added to adjust the pH for effecting the solubility and/or oxidation potential of the permanganates. This permanganate solution is impregnated into the substrate, preferably activated alumina.

The introduction of cations such as sodium, calcium, or magnesium to a potassium permanganate containing solution realizes a filter media having an effective oxidizing capability at a lower cost than that associated with the addition of permanganate in the form of sodium, calcium, or magnesium permanganate into the impregnating solution. The improved solubility of the permanganate with the introduction of one or more ions or ionic compounds allows for a greater concentration of the oxidation component within the pellet increasing the efficiency and time the filter having the filter media of the present invention can remain online prior to break through of odors. In this manner, an economical fluid filter for the continuous removal of odors, which avoids the problems of lower solubility of the more economical permanganate, potassium permanganate, in a solution impregnating an alumina-based pellet, is provided without the added costs associated with the addition of sodium, calcium, or magnesium permanganate alone, while providing a structurally sound filter media.

Nitrates are oxidants that have been found to be effective in the reduction of odors. Advantageously, the impregnating solution comprises at least one alkali metal permanganate and a water soluble nitrate salt, the composition comprising from about 0.5 to about 95.5 weight percent permanganate and from 0.5 to about 95.5 weight percent nitrate salt. In a preferred embodiment, the composition of the impregnating solution has water saturated with reactants wherein the reactants comprise from about 20 to about 75 weight percent alkali metal permanganate and from about 25 to about 80 weight percent water soluble nitrate; most preferably the reactants comprise about 33 weight percent permanganate salt and 67 weight percent nitrate salt. In both of the later more preferred embodiments, preferably the permanganate salt is added to the impregnating solution in the form of potassium permanganate and the nitrate salt is added in the form of sodium nitrate.

In a preferred aspect, the method of adding sodium ions to increase the solubility of the permanganate in the impregnating solution comprises adding sodium in the form of sodium nitrate to the impregnating solution having potassium permanganate. The combination of potassium permanganate and sodium nitrate is synergistic in removal of odors from a gas stream. Potassium permanganate is typically soluble in water under saturated conditions at about 4% at room temperature while sodium permanganate is typically over 40% soluble in water at room temperature. However, the solubility of potassium permanganate can be increased to be in excess of 12% (wt/v) or even upwards to over 20% (wt/v) with the addition of sodium nitrate. In addition to providing increased solubility of permanganate in the impregnating solution, the nitrates are impregnated into the alumina substrate. Thus, the addition of potassium permanganate and sodium nitrate provides an impregnating solution having permanganate at increased levels compared to those provided with the introduction of potassium permanganate alone; and in addition a second oxidizer, nitrate is also provided. This increase in solubility and the incorporation of nitrates provides a highly effective and efficient oxidizing solution for impregnating into filter media. It is important to note that the addition of permanganate into the impregnating solution can be done with permanganate salts in addition to the potassium permanganate salt such as sodium permanganate and be within the scope of the present invention. Preferably, the permanganate and the nitrate are maintained in the impregnating solution in a ratio of at least 1:1 to about 4:1. Advantageously the permanganate is added to the impregnating solution until saturation is achieved. Advantageously, in one embodiment of the impregnating solution, the solution comprises from about 0.5 to about 20 weight percent potassium permanganate, from about 0.5 to about 42 weight percent sodium nitrate, and from about 48 to about 99 weight percent water. In another aspect, the aqueous composition comprises from about 4 to about 16 weight percent potassium permanganate, from about 8 to about 33 weight percent sodium nitrate and from about 59 to about 88 weight percent water. In yet another embodiment, an impregnating solution has a quantity of sodium nitrate in an aqueous solution with a pH adjusted as necessary to maximize the solubility and reactivity of the potassium permanganate therein, and the solution is saturated with permanganate. It is to be understood that other permanganate salts such as sodium permanganate may be added to the impregnating solution in conjunction with the potassium permanganate and be within the scope of the instant invention.

Sodium phosphate and combinations of sodium phosphate and sodium nitrate have also been found to be effective in increasing the solubility of the permanganate introduced into the impregnating solution in the form of potassium permanganate. An amount of sodium bicarbonate has also been found to be an effective solubilizing agent of permanganate. An impregnating solution having an amount of potassium permanganate and either or both sodium phosphate and sodium nitrate in combination with sodium bicarbonate has also found to be effective. It is understood that ions and ionic compounds selected from the group consisting of $Na^+$, $Li^+$, $K^+$, $NH_4^+$, $Mg^{2+}$, $Ca^{2+}$, $Cl^-$, $SO_4^{2-}$, $BO_3^{2-}$, $CO_3^{2-}$, $PO_4^{3-}$, $NO_3^-$, and combinations thereof in conjunction with an amount of potassium permanganate in an impregnating solution are within the scope of the present invention.

The impregnating solution is used for impregnating a base or support material such as activated alumina such as alumina trihydrate. One method involves providing ground activated alumina, commercially available, capable of at least partial rehydration. The ground activated alumina is then mixed with the impregnating solution having permanganate and preferably sodium salts to obtain a composite mixture comprising an alumina material containing permanganate substantially uniformly distributed throughout. The composite mixture may be rehydrated and partially cured to provide desired strength and abrasion resistance in the alumina containing media to be formed without filling pores in the substrate to an extent that would be detrimental to the reactivity of the pellet with odorous materials in the fluid passed there through. The impregnated alumina can be pelletized or shaped as desired by any suitable method known by persons having ordinary skill in the art. For example, the impregnated alumina can be agglomerated by extrusion, compaction (as in a briquetting press) or by tumbling. A method of pelletizing is to tumble the alumina with the impregnating solution to cause the production of rounded pellets. Round pellets of filter media are preferred because the geometrical configuration provides low resistance to flowing fluid streams and a substantial exposed surface area contacting the fluid stream and therefore a low pressure drop across the filter media is achieved with a high rate of reaction. Moreover, the round configuration provides good resistance to abrasion which minimizes wear on the pellets. A preferred method of pelletizing is to compress granules in a compression forming machine. This method has the advantage of providing tablets in circumstances where reactive surface area is of higher importance, spheres, saddles, raschig rings, cross partition rigs, pall rings, cascade rings, and the like may be formed with a compression forming machine as well as rounded or oval tablets. Preferably, a compression forming machine is set to have a compression ratio between about 2 to 5 and more preferably between about 3.15 to 3.40. After pelletization, the partially hydrated pellets may be left undisturbed or heated in a humidified atmosphere to allow for the completion of the hydration reaction to utilize uncombined water within the compressed pellet or replenishing moisture to obtain desired physical and chemical properties of the finished media. As such, this final step completes the curing of the media.

Another step is the preparation of the impregnating solution having the permanganate. Preferably, an aqueous impregnating solution of one or more ions or ionic compounds such as $NO_3^-$, $Na^+$, $Li^+$, $K^+$, $Cl^-$, $SO_4^{2-}$, $BO_3^{2-}$, $CO_3^{2-}$, $PO_4^{3-}$, $SO_3^{2-}$, $NH_4^+$, $Mg^{2+}$, and $Ca^{2+}$ is prepared and stirred while potassium permanganate is added until the solution is saturated. However, it is important to note that the addition of $Mg^{2+}$ or $Ca^{2+}$ with $CO_3^{2-}$, as carbonate or bicarbonate, or $Mg_2^+$ or $Ca_2^+$ with $SO_4^{2-}$, as sulfate or bisulfate, or $Mg^{2+}$ or $Ca^{2+}$ with $PO_4^{3-}$, as phosphate or other causes undesired precipitation of $MgCO_3$, $CaCO_3$, $Mg_3(PO_4)_2$, $Ca_3(PO_4)_2$, $MgSO_3$, or $CaSO_3$, therefore these combinations are to be avoided. An amount of other permanganate salts may also be added. Preferably, an amount of ions or ionic compounds are present in the solution in a quantity sufficient to achieve a solubility of permanganate in the solution of at least 12 g per 100 ml and more preferably 40 g per 100 ml of solution at room temperature. Advantageously the temperature of the solution is maintained over 30° C., preferably in a range of about 90° C. to 95° C., further increasing the solubility of the permanganate in the solution. Other reagents can be added to the impregnating solution for additional odor removal capabilities.

The substrate may then be impregnated with the impregnating solution by mixing the impregnating solution and the activated alumina substrate in a tumbling mill where spray nozzles introduce the impregnating solution. The agglomerating effect of the impregnating solution agglomerates the substrate into spherical or oval pellets. The feed rates of the substrate and impregnating solution as well as the rate of revolution of the tumbling mill is controlled to produce pellets having a desired size. Alternatively, media may be formed with a compression forming machine. When the media is compression formed, the impregnating solution and activated alumina are mixed and allowed to partially cure in a heated humid environment providing a coherent mass. The coherent mass is ground into granules, preferably having a particle size of about 40 to 80 mesh, and compressed into a desired shape. Curing is then completed forming media having a desired strength. The media may also be formed by other methods as is known in the art wherein curing can be accomplished before, during, and/or the formation of the pellet, tablet, or other configured media.

The impregnated alumina containing media may then be cured to insure a desired density and strength. The degree of curing (before, during, or after shaping of the media) depends upon desired properties such as strength of the media and pore volume. A satisfactory set of conditions for curing of the formed media is to cure for about 4 hours at about 55-60° C., up to a maximum of 99.9° C., in a humid environment. Hydrating the media while allowing the removal of any uncombined water during the curing process has been found to provide abrasive resistant media. However, hydration may not be necessary and as such the humidity during the curing stage may be reduced.

This method provides a permanganate-alumina composite filter media wherein the permanganate oxidizers are substantially uniformly distributed throughout the oxidizing media.

EXAMPLES

Example 1

Tablet-shaped gas phase media was made by placing 15 g. $KMnO_4$, 15 g. $NaHCO_3$, and 10 g. $NaNO_3$ in a solution tank. 100 g. of activated alumina (AA) was placed in a dry powder mixer. 100 g. of water was added to the solution tank and heated to about 90° C. to 95° C. wherein the $KMnO_4$, $NaHCO_3$, and $NaNO_3$ was dissolved forming an ionic solution. The AA was mixed into the ionic solution and cured at about 50° C. until the moisture was between about 26% to 32%. The cured mixture was granulated into uniform granules while the moisture was maintained between about 26% to 32%. The granules were quickly placed into a compression forming machine having been set with a compression ratio between about 3.15 to 3.40. The granules were compressed into tablets. The tablets were cured in a humidifier oven at about 50° C. to 60° C. until the tablets contained between about 15% to 20% free water by weight.

Examples 2-15

Figure 1:
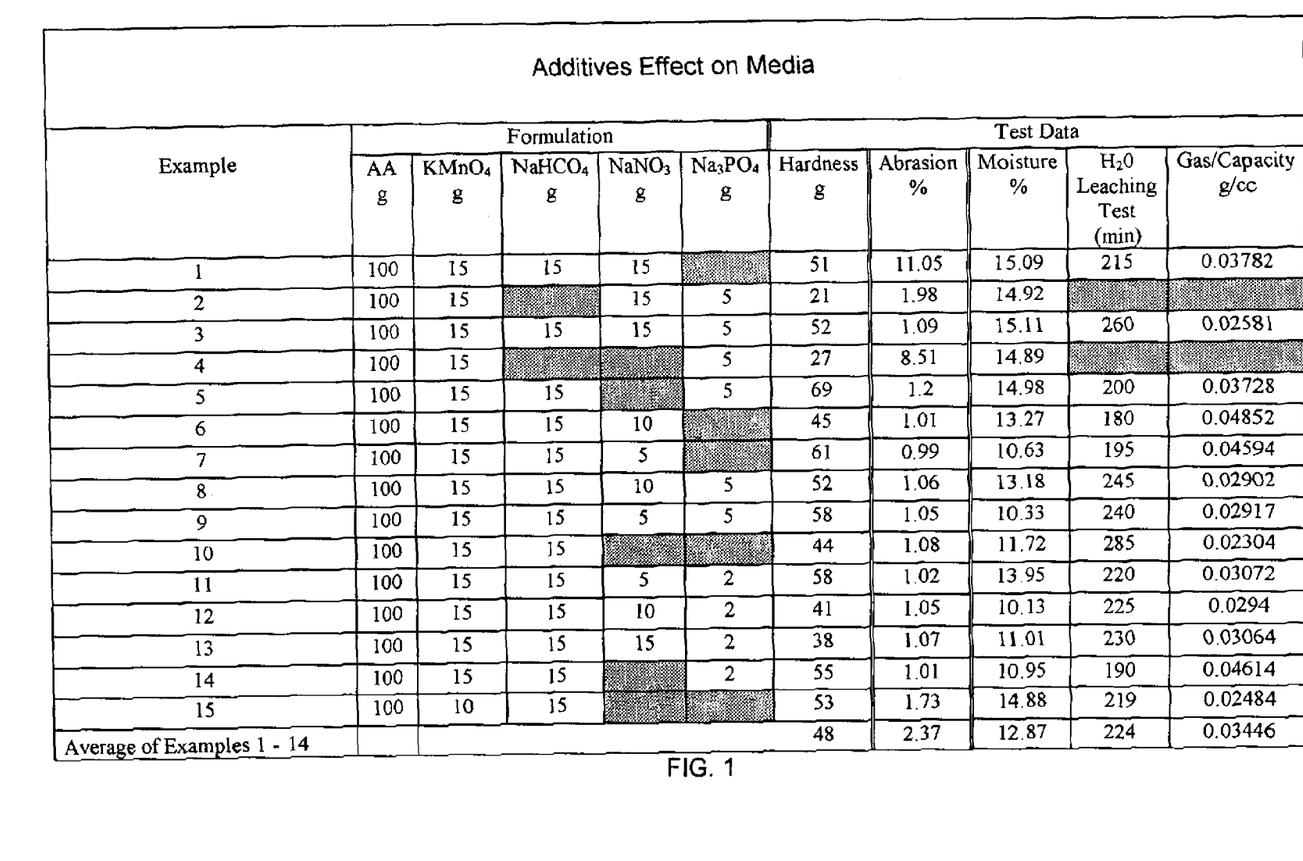
FIG. 1 is a table of test data generated in the Examples showing performance characteristics of several embodiments of the filtration media of the present invention as compared with the prior art.

Tablets were made according to the process of Example 1 wherein varying amounts of $NaNO_3$ and $Na_3PO4$ were introduced into the solution tank as indicated in the table of FIG. 1.

The pellets formed in examples 1-15 were tested to determine hardness, % abrasion, moisture content, and optionally water leaching and gas capacity according to the following procedures.

Hardness of the pellets formed in examples 1-15 was determined by using an YPD-200C sclerometer. The sclerometer utilizes a motor to transmit a force to press the tablet and causes the bridge of a sensor to amplify the pressure signal, which in turn is used to calculate a hardness value through the A/D transfer circuit. Ten samples of pieces of granular or pelletized media were taken at random from the media of each example as separate batches to test the hardness of each. Each batch was placed in turn on the center of the datum plate and the "start" key was pressed. The display value at the time the tablets of the batch had been crushed is the hardness of that example. This was repeated for the batch of tablets of each example, the results of which are in the table of FIG. 1.

Abrasion of the pellets formed in examples 1-15 was determined by using a pharmaceutical tablet brittleness measurement instrument measuring the resistance of granular or pelletized media to abrasion. Wheel cavity hubs contained a measured mass of tablets from each example in turn, which were rotated at a specified speed for a prescribed number of cycles. After the prescribed number of cycles, the media was separated from the smaller pieces and the mass of media was determined again. The difference in masses is indicative of the abrasion resistance of the media. The tablets of each example were separately tested.

Samples of twenty pieces of granular or pelletized media were taken at random from the media of each example as separate batches to calculate the abrasion resistance. The batch from each example was weighed, accurate to 0.0001 g, and recorded, $W_1$. Each batch was separately placed into wheel hubs carefully so that there was no breakage of the media via rough handling. The tablet brittleness measurement instrument was turned on to start rotating the wheel cavity hubs containing the batch at 25 RPM. After 100 rotations, the wheel hubs automatically stopped rotating, then the hubs were opened and intact tablets were carefully removed. The dust was blow off the surface of these intact tablets. The intact tablets were again weighed, accurate to 0.0001 g, and the weight was recorded as $W_2$. Any small pieces of broken off media observed was also included in $W_2$. The abrasion of each batch of tablets from each example was then calculated according to the following formula.

$$\text{Abrasion} = \frac{W_1 - W_2}{W_1} * 100\%$$

Moisture content of the pellets formed in examples 1-15 was determined by a weighing-drying method in which the samples were dried until their mass is constant. At the start of the measurement a Moisture Analyzer was used to determine the weight of the sample, the sample was then quickly heated by integral halogen heating module and the moisture vaporized. During the drying process, the instrument continually measured the weight of the sample. Once drying was completed, the moisture content was determined by a differential weighing before and after drying. A batch random sample was taken from the media of each example. Each batch was separately placed into the Moisture Analyzer in turn and the set up key was pressed and the temperature was set to 105° C. for drying the sample. The set up key was pressed and standard drying mode was selected. The Tare/zero key was pressed to tare the balance. The heating module was opened and a batch sample was placed on the sample pan. The wet weight (WW) of the batch sample was shown on the screen and recorded. To obtain the best results, the wet weight of the batch sample was between about 5 g to 8 g, and sample was distributed evenly over the sample pan. The heating module was closed and the instrument automatically began the drying and measuring process. After the mass of the batch sample got constant, a dry weight (DW) was recorded and the moisture content (MC) was calculated automatically according to the following formula:

$$MC\% = \frac{\text{Wet weight}(WW) - \text{Dry weight}(DW)}{\text{Wet Weight}(WW)} \times 100\%$$

The heating module was opened and the next batch sample was analyzed.

Water leaching capacity of pellets formed in selected examples 1-15 was determined by randomly sampling 10 grams of pellets formed in the selected examples. Each sample was placed individually into a 250 ml. cone shaped beaker where water was introduced at a flow rate of 350 ml./min into each beaker. The time taken for the water to flow clear in each beaker was recorded in minutes. The pellets were analyzed to determine if they were suitable for gas capacity testing. This analysis comprised of first determining if the pellet had sufficient strength to maintain integrity in the water bath and by crushing pellets from each sample to determine if a purple color remained within the pellet indicating insufficient penetration of the water within the pellet.

Gas capacity of pellets from selected examples was determined by evaluating the capacity of removal of various virgin, newly impregnated or in-service, granular or pelletized media when subjected to a flowing gas stream containing high level of contaminants, under the laboratory test conditions. Breakthrough capacity was determined by passing a stream of tempered, humidified air containing 1 volume % contaminant through a sample of granular or pelletized media of known volume under specified conditions until the concentration of contaminant in the effluent gas reaches 50 ppm. The air utilized was tempered, humidified, clean, oil-free and compressed. The contaminant gas contained 5% contaminant such as $H_2S$, $Cl_2$, $SO_2$, $NH_3$, etc. in nitrogen. Media was sampled at random from pellets of each of the selected examples to be tested yielding an individual sample from each selected example. The apparent density of each sample was determined. The contaminant and air flow rates were adjusted to generate a 1.0% (vol./vol.) contaminant gas stream at a total flow rate of 1450 $cm^3$/min through a one-inch diameter adsorption tube. The absorption tube was cleaned, dried, and tared to the nearest 1.0 mg. The absorption tube was slowly filled with 116 mL of media sampled from one example while it was tapped to insure that the media settled into the tube with minimal voids with the media. The adsorption tube contains 116 mL when filled and had a bed depth of approximately 22.9 cm. The filled absorption tube was weighed to the nearest 1.0 mg. The filled absorption tube was then transferred to the test system and connected to the test apparatus so that contaminated gas entered the bottom of the tube and flowed through the filtration media where it was then analyzed by a SPM (Single Point Monitor) gas detector from Honeywell Zellweger Analytics. When the breakthrough of 50 ppm was indicated, the time elapsed from the start to 50 ppm breakthrough was recorded. This was repeated for each sample from each selected example and the gas capacity was calculated for each selected example according to the following equation.

$$\text{Gas Capacity}(GM/CC) = \frac{(K \times 10^{-5})(C)(F)(T_b)}{V}$$

Where:
K=1.52 for $H_2S$, 2.86 for $SO_2$, 3.17 for $Cl_2$, 2.15 for $CH_3SH$, 0.76 for $NH_3$, 2.05 for $NO_2$, and 1.39 for NO.
C=Concentration of the contaminate gas in airstream, Volume %.
F=Total stream flow rate, cc/min
$T_b$=Time to 50 ppm breakthrough, minutes.
V=Volume of the adsorption tube media column, cc.

The results of Examples 1-15 are tabulated in the table of FIG. 1. It is important to note that these examples are only selected embodiments of the present invention and are not to serve as limiting the ions or concentrations thereof that may be introduced into the impregnating solution as other and different ions or ionic compounds and concentrations thereof are within the scope of the present invention. For example, a portion of the permanganate may be introduced into the impregnating solution in the form of sodium permanganate or other permanganate salts and be within the scope of the present invention.

Example 15, having no $NaNO_3$ or $Na_3PO_4$, is that of the prior art and serves as a baseline for comparison with examples of filter media of the present invention produced by the process steps of the present invention. As shown in the table in FIG. 1, the average gas capacity of the selected examples of media is about 0.0345 g./cc while that of the prior art is only about 0.0248 g./cc. Several embodiments were shown to have a gas capacity in excess of 33% more than the media of the prior art allowing a gas filter cartridge, bulk media, media mechanically or adhesively attached to a substrate such as a foam, wire, synthetic fibers, and fiberglass, or media contacted with a fluid stream by other means as is known by persons having ordinary skill in the art having the same volume of filter media to have a one third increase in time filtering a gas stream. Additionally, the hardness and abrasion results were shown to be acceptable for most embodiments, many of which show a significant improvement over the prior art.

Figure 2:
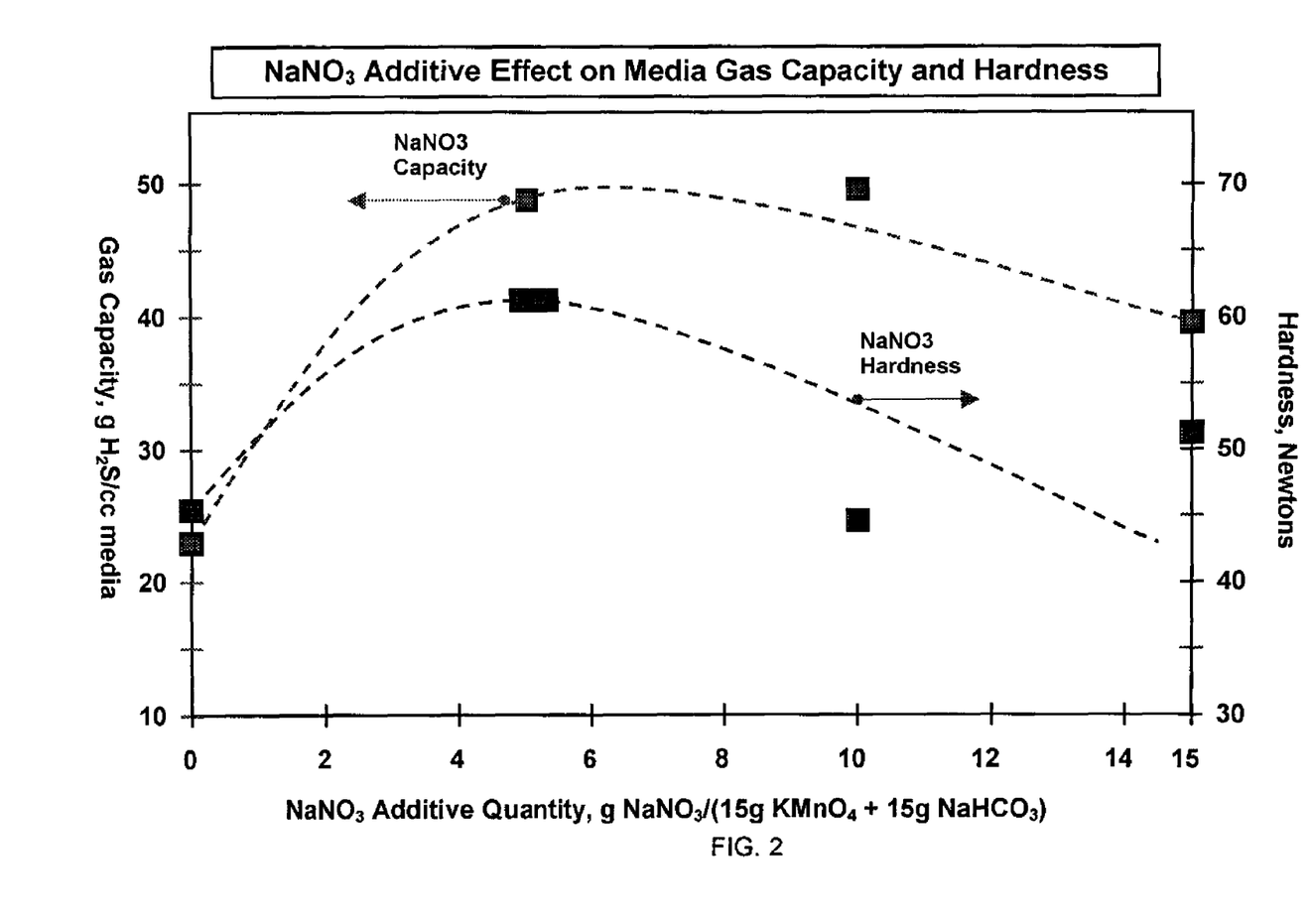
FIG. 2 is a graphical view of selected data of selected embodiments of the present invention having $NaNO_3$.
Figure 3:
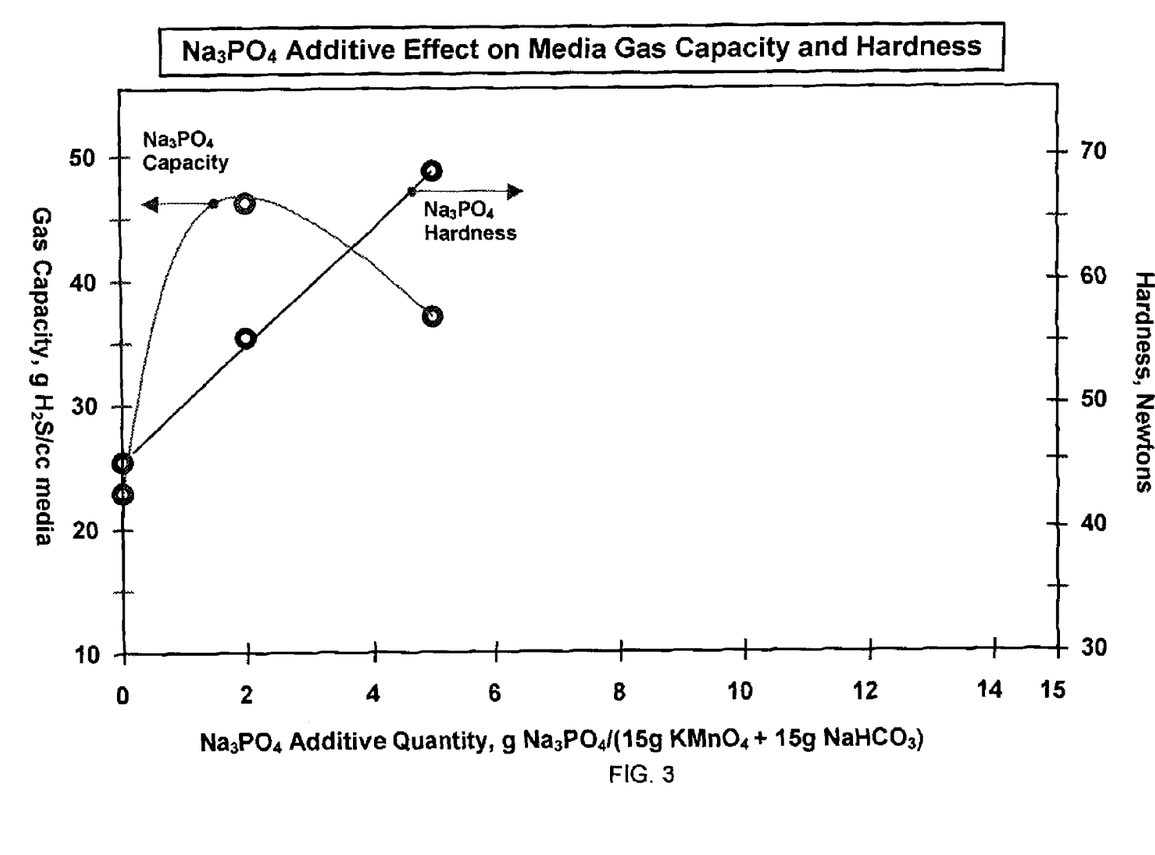
FIG. 3 is a graphical view of selected data of selected embodiments of the present invention having $Na_3PO_4$.

FIGS. 2 and 3 graphically show the effect on gas capacity and hardness as a function of concentrations of $NaNO_3$ and $Na_3PO_4$ respectively. FIG. 2 shows that the gas capacity of pellets with 15 g. $KMnO_4$ and 15 g. $NaHCO_3$ and varying amounts of $NaNO_3$, as in Examples 1, 6, 7 and 10. An optimum amount of $NaNO_3$ is estimated to be between about 2 and 8 g. or advantageously approximately 5 g. as the capacity and hardness curves are shown to reach desired levels within this range. The tablets of Example 7 in Table 1 have 15 g. $KMnO_4$, 15 g. $NaHCO_3$, and 5 g. $NaNO_3$ and exhibit a gas capacity of 0.046 g. $H_2S/cc$ and a hardness of 61 g., which is a significant increase in both gas capacity and hardness as compared to Example 10 having no $NaNO_3$. However, amounts of $NaNO_3$ lower than 2 g. may provide desirable pellet characteristics and are considered to be within the scope of the present invention.

FIG. 3 graphically shows the effect on gas capacity and hardness as a function of concentration of $Na_3PO_4$. FIG. 3 shows that the gas capacity of pellets with 15 g. $KMnO_4$ and 15 g. $NaHCO_3$ and varying amounts of $Na_3PO_4$, as in Examples 5, 10 and 14. An optimum amount of $NaHCO_3$ is estimated to be between about 0.1 and 4 g. or advantageously approximately 2 g. as the capacity and hardness curves are shown to reach desired levels within this range. The tablets of Example 14 in Table 1 have 15 g. $KMnO_4$, 15 g. $NaHCO_3$, and 2 g. $NaHCO_3$ and exhibit a gas capacity of 0.046 g. $H_2S/cc$ and a hardness of 55 g. which is a significant increase in both gas capacity and hardness as compared to Example 10 having no $NaHCO_3$. However, amounts of $NaHCO_3$ lower than 0.1 g. may provide desirable pellet characteristics and are considered to be within the scope of the present invention.

Figure 4:
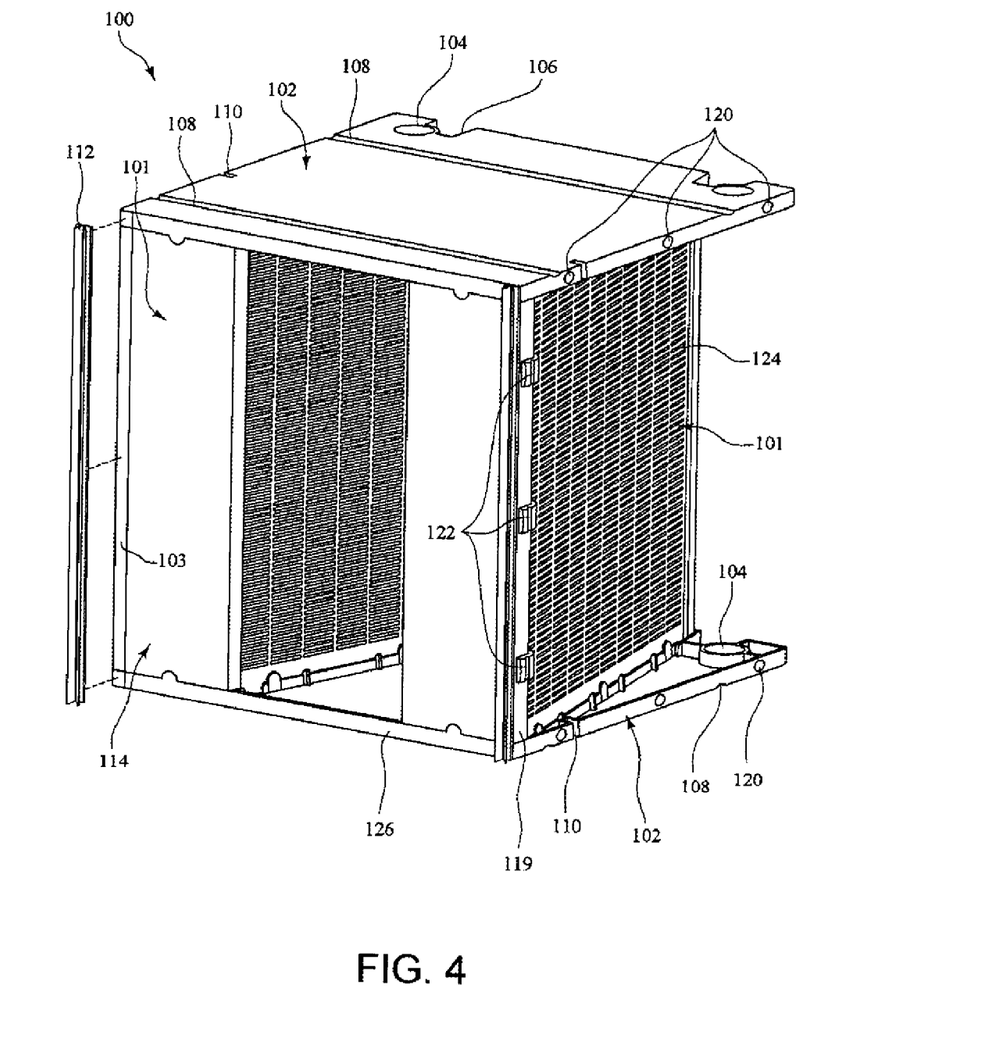
FIG. 4 is a perspective view of an embodiment of a filter cassette having a configuration for placement within a gas flow stream.

The filtration media of the present invention may be placed in a cassette or container for use such as the porous cartridge filled with loosely packed oxidizing pellets shown in FIG. 4. FIG. 4 shows "V" shaped cartridge filter cassette 100. It is to be understood that this cartridge is but one example of a filtering container which may house the filtration media having a chemical reagent as other containers known in the art may be used to house the media of the present invention. For instance the media having a chemical reagent of the present invention may be used in bulk form, mechanically or adhesively attached to a substrate such as a foam, wire, synthetic fibers, and fiberglass, or contacted with a fluid stream by other means as is known by persons having ordinary skill in the art. Filter cassette 100 is an example of a media container for treating an air stream and has rectangular side panels 102 with a pair of filter media containers 101 extending there between. Each filter media container 101 is formed with opposing rectangular end plates 114 and rear end plates (not shown) and a pair of opposing rectangular media screens 124. The pair of filter media containers 101 are in a "V" configuration with outermost end plates 114 on a sealing side of cassette 100 extending between corners of side panels 102. The sealing side of filter cassette 100 is substantially smooth, flat, and substantially uniform surface and is formed with front end plates 114 and sealing edges 126 of side panels 102. End plates 114 and side panel edges 126 optionally have an indentation 103 extending between the outer edges of side panels 102 and are preferably substantially parallel and proximate the outer longitudinal edges of end plates 114. Seal location indentations 103 may have a seal 112 inserted therein. Seal 112 preferably will be a butterfly seal or a gel seal. Friction reducers 122 on outer edges 119 of end plates 114 are optional and are shown here in the form of a clip having a groove on an outer surface substantially perpendicular to rectangular side panels 102 which engage a guide in a housing or rack. Guide notches 110 in the side edges of side panels 102 are in the sides other than the sealing and non-sealing sides having front end plates 114 and rear end plates respectively. Side panels 102 optionally have at least one gasket locator indentation 108 therein in strip form extending between the outer edges of side panels 102 substantially parallel to the sealing surface of cassette 100. Preferably a gasket such as a compression gasket is in each gasket locator indentation 108. Optionally, rectangular side panels 102 each have at least one friction reducer 120 in the sides other than the sealing and said non-sealing sides. In the embodiment shown, side panels 102 each have finger holes 104 proximate corners adjacent the non-sealing side of cassette 100. Also shown here are notches 106 in side panels 102 proximate and circumscribing a portion of finger holes 104.

The invention claimed is:

1. A method of producing a filtration media having a chemical reagent comprising the steps of:
   mixing $H_2O$, $KMnO_4$, and at least one salt adding ions or ionic compounds selected from the group consisting of $Na^+$, $Li^+$, $K^+$, $NH_4^+$, $Cl^-$, $SO_4^{2-}$, $BO_3^{2-}$, $CO_3^{2-}$, $PO_4^{3-}$ $NO_3^-$ and combinations thereof or from the group consisting of $Na^+$, $Li^+$, $K^+$, $NH_4^+$, $Mg^{2+}$, $Ca^{2+}$, $Cl^-$, $BO_3^{2-}$, $NO_3^-$ and combinations thereof forming an impregnating solution;
   heating said impregnating solution;
   combining an activated alumina support with said impregnating solution in an amount sufficient to form a coherent mass;
   mixing and heating said impregnating solution and said activated alumina support; and
   curing said impregnating solution and said activated alumina support forming said coherent mass;
   wherein said at least one salt has $NaNO_3$ and $Na_3PO_4$.

2. A method of producing a filtration media having a chemical reagent comprising the steps of:
   mixing $H_2O$, $KMnO_4$, and at least one salt adding ions or ionic compounds selected from the group consisting of $Na^+$, $Li^+$, $K^+$, $NH_4^+$, $Cl^-$, $SO_4^{2-}$, $BO_3^{2-}$, $CO_3^{2-}PO_4^{3-}$ $NO_3^-$ and combinations thereof or from the group consisting of $Na^+$, $Li^+$, $K^+$, $NH_4^+Mg^{2+}$, $Ca^{2+}$, $Cl^-$, $BO_3^{2-}$ $NO_3^-$ and combinations thereof forming an impregnating solution;
   heating said impregnating solution;
   combining an activated alumina support with said impregnating solution in an amount sufficient to form a coherent mass:
   mixing and heating said impregnating solution and said activated alumina support; and
   curing said impregnating solution and said activated alumina support forming said coherent mass wherein said at least one salt has $NaNO_3$ and $Na_3PO_4$ wherein said impregnating solution has a ratio of $KMnO_4$, $NaHCO_3$, and $NaNO_3$ in a range between 15:15:2 and 15:15:8.

3. A method of producing a filtration media having a chemical reagent comprising the steps of:
   mixing $H_2O$, $KMnO_4$, and at least one salt adding ions or ionic compounds selected from the group consisting of $Na^+$, $Li^+$, $K^+$, $NH_4^+$, $Cl^-$, $SO_4^{2-}$, $BO_3^{2-}$, $CO_3^{2-}PO_4^{3-}$ $NO_3^-$ and combinations thereof or from the group consisting of Na$^+$, Li$^+$, K$^+$, NH$_4^+$, Mg$^{2+}$, Ca$^{2+}$, Cl$^-$, BO$_3^{2-}$, NO$_3^-$ and combinations thereof forming an impregnating solution;

heating said impregnating solution;

combining an activated alumina support with said impregnating solution in an amount sufficient to form a coherent mass;

mixing and heating said impregnating solution and said activated alumina support; and curing said impregnating solution and said activated alumina support forming said coherent mass wherein said at least one salt has NaNO$_3$ and Na$_3$PO$_4$, wherein said impregnating solution has KMnO$_4$, NaHCO$_3$, and NaNO$_3$ in a ratio of about 3:3:1.

4. A method of producing a filtration media having a chemical reagent comprising the steps of:

mixing H$_2$O, KMnO$_4$, and at least one salt adding ions or ionic compounds selected from the group consisting of Na$^+$, Li$^+$, K$^+$, NH$_4^+$, Cl$^-$, SO$_4^{2-}$, BO$_3^{2-}$, CO$_3^{2-}$, PO$_4^{3-}$, NO$_3^-$ and combinations thereof or from the group consisting of Na$^+$, Li$^+$, K$^+$, NH$_4^+$, Mg$^{2+}$, Ca$^{2+}$, Cl$^-$, BO$_3^{2-}$, NO$_3^-$ and combinations thereof forming an impregnating solution;

heating said impregnating solution;

combining an activated alumina support with said impregnating solution in an amount sufficient to form a coherent mass;

mixing and heating said impregnating solution and said activated alumina support; and curing said impregnating solution and said activated alumina support forming said coherent mass wherein said at least one salt has NaNO$_3$ and Na$_3$PO$_4$, wherein said impregnating solution has a ratio of KMnO$_4$, NaHCO$_3$, and Na$_3$PO$_4$ in a range between 15:15:0.1 and 15:15:4.

5. The method of producing a filtration media of claim 4 wherein said impregnating solution has KMnO$_4$, NaHCO$_3$, and Na$_3$PO$_4$ in a ratio of about 15:15:2.

* * * * *

UNITED STATES PATENT AND TRADEMARK OFFICE
CERTIFICATE OF CORRECTION

| | |
|---|---|
| PATENT NO. | : 7,906,456 B2 |
| APPLICATION NO. | : 11/627465 |
| DATED | : March 15, 2011 |
| INVENTOR(S) | : Michael W. Osborne et al. |

It is certified that error appears in the above-identified patent and that said Letters Patent is hereby corrected as shown below:

Replace drawing sheet 1 containing Figure 1 with the attached replacement drawing sheet containing Figure 1.

Signed and Sealed this
Twenty-third Day of February, 2016

Michelle K. Lee
*Director of the United States Patent and Trademark Office*

Additives Effect on Media

| Example | Formulation | | | | | | Test Data | | | | |
|---|---|---|---|---|---|---|---|---|---|---|---|
| | AA g | $KMnO_4$ g | $NaHCO_3$ g | $NaNO_3$ g | $Na_3PO_4$ g | Hardness g | Abrasion % | Moisture % | $H_2O$ Leaching Test (min) | Gas/Capacity g/cc |
| 1 | 100 | 15 | 15 | 15 | | 51 | 11.05 | 15.09 | 215 | 0.03782 |
| 2 | 100 | 15 | | 15 | 5 | 21 | 1.98 | 14.92 | 260 | 0.02581 |
| 3 | 100 | 15 | 15 | 15 | 5 | 52 | 1.09 | 15.11 | 200 | 0.03728 |
| 4 | 100 | 15 | 15 | 15 | 5 | 27 | 8.51 | 14.89 | 180 | 0.04852 |
| 5 | 100 | 15 | 15 | | 5 | 69 | 1.2 | 14.98 | 195 | 0.04594 |
| 6 | 100 | 15 | 15 | 10 | | 45 | 1.01 | 13.27 | 245 | 0.02902 |
| 7 | 100 | 15 | 15 | 5 | 5 | 61 | 0.99 | 10.63 | 240 | 0.02917 |
| 8 | 100 | 15 | 15 | 10 | 5 | 52 | 1.06 | 13.18 | 285 | 0.02304 |
| 9 | 100 | 15 | 15 | 5 | | 58 | 1.05 | 10.33 | 220 | 0.03072 |
| 10 | 100 | 15 | 15 | 5 | 2 | 44 | 1.08 | 11.72 | 225 | 0.0294 |
| 11 | 100 | 15 | 15 | 10 | 2 | 58 | 1.02 | 13.95 | 230 | 0.03064 |
| 12 | 100 | 15 | 15 | 15 | 2 | 41 | 1.05 | 10.13 | 190 | 0.04614 |
| 13 | 100 | 15 | 15 | | 2 | 38 | 1.07 | 11.01 | 219 | 0.02484 |
| 14 | 100 | 15 | 15 | 15 | | 55 | 1.01 | 10.95 | 224 | 0.03446 |
| 15 | 100 | 10 | 15 | 15 | | 53 | 1.73 | 14.88 | | |
| Average of Examples 1 - 14 | | | | | | 48 | 2.37 | 12.87 | | |

FIG. 1